United States Patent
Gupta

(10) Patent No.: US 7,059,191 B2
(45) Date of Patent: Jun. 13, 2006

(54) DETERMINING DEFECTIVE DEVICES WHICH GENERATE SOUND DURING OPERATION

(75) Inventor: Ajay Gupta, Bhilai (IN)

(73) Assignee: Texas Instruments Incorporated, Dallas, TX (US)

( * ) Notice: Subject to any disclaimer, the term of this patent is extended or adjusted under 35 U.S.C. 154(b) by 771 days.

(21) Appl. No.: 10/196,912

(22) Filed: Jul. 17, 2002

(65) Prior Publication Data

US 2003/0061034 A1 Mar. 27, 2003

Related U.S. Application Data

(60) Provisional application No. 60/323,710, filed on Sep. 21, 2001.

(51) Int. Cl.
*G01N 29/00* (2006.01)

(52) U.S. Cl. .............................. 73/587; 73/602; 73/659

(58) Field of Classification Search .................. 73/587, 73/649, 659, 660, 602, 579, 599; 702/179, 702/180, 182, 183, 184
See application file for complete search history.

(56) References Cited

U.S. PATENT DOCUMENTS

| | | | | |
|---|---|---|---|---|
| 4,429,578 A * | 2/1984 | Darrel et al. | ................ | 73/659 |
| 5,144,838 A * | 9/1992 | Tsuboi | ........................ | 73/579 |
| 5,377,275 A * | 12/1994 | Suzuki | ..................... | 381/71.5 |
| 5,445,027 A * | 8/1995 | Zorner | ........................ | 73/593 |
| 5,511,422 A * | 4/1996 | Hernandez | .................... | 73/593 |
| 5,679,900 A * | 10/1997 | Smulders | ..................... | 73/659 |
| 5,710,715 A * | 1/1998 | Shitanda | ..................... | 702/56 |
| 5,922,963 A * | 7/1999 | Piety et al. | ................... | 73/659 |
| 5,955,674 A * | 9/1999 | McGovern et al. | ........... | 73/650 |
| 6,925,879 B1 * | 8/2005 | Raichle | ..................... | 73/579 |

OTHER PUBLICATIONS

Pending U.S. Appl. No. 09/517,986; filed March 3, 2000; entitled *Page Address Look-Up Range RAM;* Inventor: David R. Matt (Texas Instruments Incorporated TI-29809).

* cited by examiner

*Primary Examiner*—Hezron Williams
*Assistant Examiner*—Jacques Saint Surin
(74) *Attorney, Agent, or Firm*—Robert D. Marshall, Jr.; W. James Brady; Frederick J. Telecky, Jr.

(57) ABSTRACT

Determining whether a device is defective by analyzing the sound signals generated by the device. Digital samples are generated to represent the sound signals. Digital samples are transformed from the time domain to the frequency domain to generate a frequency spectrum. By comparing the levels of intensity at a corresponding frequency to the threshold levels of intensity, defective devices can be determined.

22 Claims, 5 Drawing Sheets

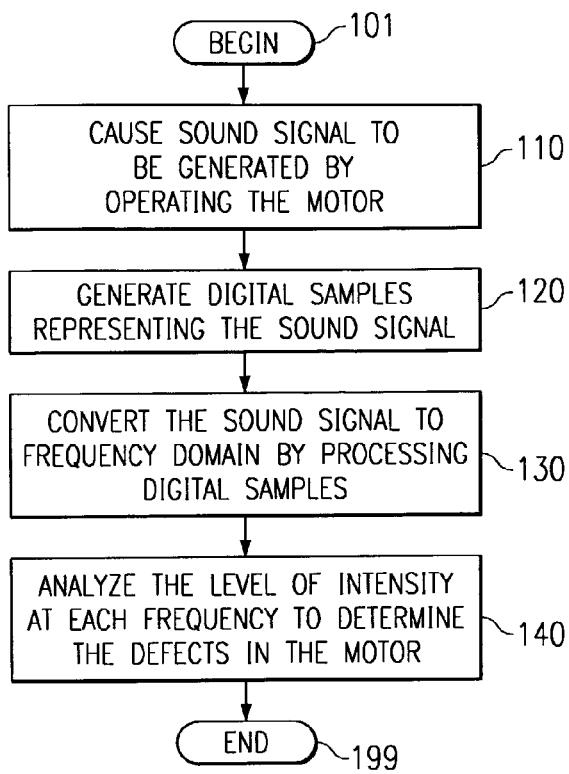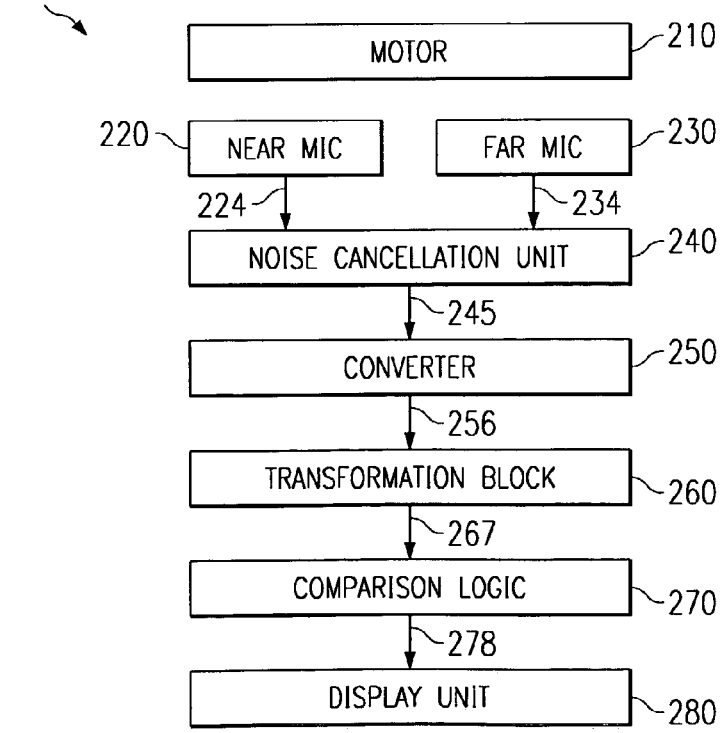

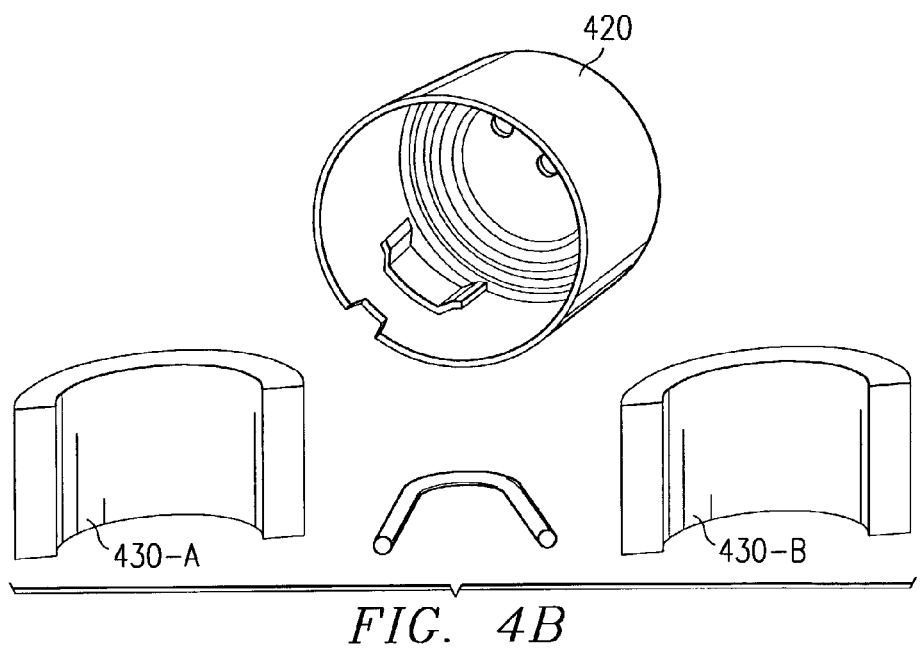
FIG. 4B
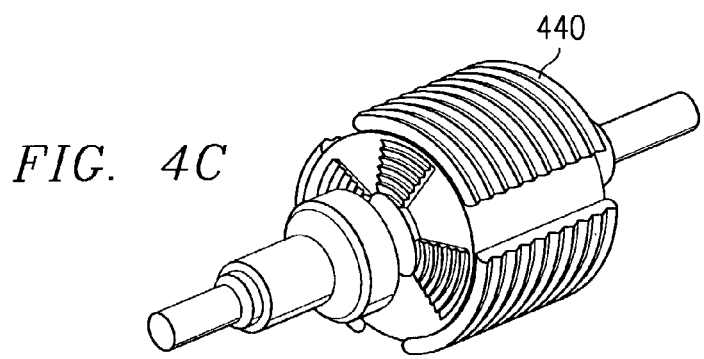
FIG. 4C
FIG. 5A
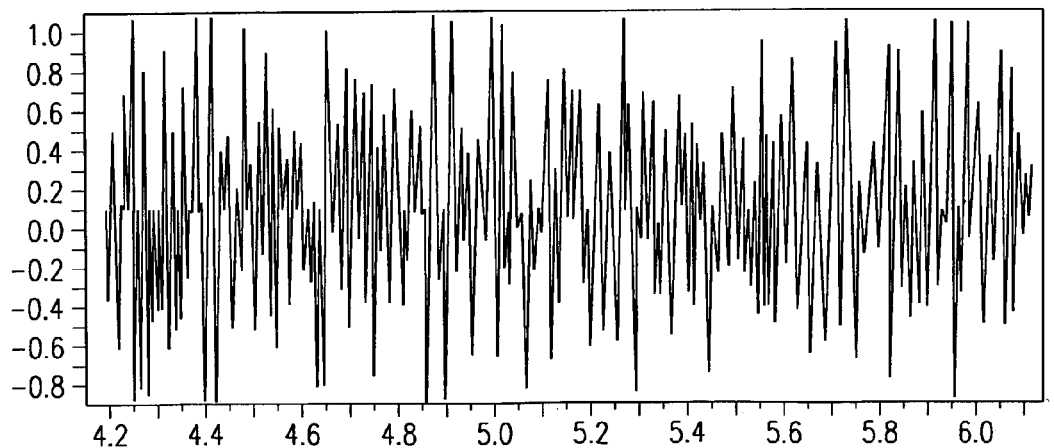

DETERMINING DEFECTIVE DEVICES WHICH GENERATE SOUND DURING OPERATION

This application claims priority under 35 USC §119(e)(1) of Provisional Application No. 60/323,710, filed Sep. 21, 2001.

BACKGROUND OF THE INVENTION

1. Field of the Invention

The present invention relates to electronic testing systems, and more specifically to a method and apparatus for determining whether a device is defective.

2. Related Art

Devices are often tested by listening to the sound generated during operation (of the device). Typically, an expert listens to the sound generated by a device and determines whether the device is defective.

One problem with such an approach is that the procedure is subject to human errors (particularly if people with limited experience are employed), and can also be time consuming. In addition, for better determination results, an expert may be needed at each location where testing is performed, which may add to the overall cost of production.

Accordingly, a manufacturer may test only a few samples of a batch (of manufactured devices), and determine to either accept or reject the entire batch depending on the results of testing. As each device is not tested individually, non-defective devices may also be rejected, which is generally undesirable.

Additional problems may be encountered in environments where noise is present around the testing areas. For example, areas in which motors are manufactured and also tested, may contain high levels of noise. The noise components may interfere with the sound generated by the device, and human beings may be unable to accurately analyze the noise generated by the devices in the presence of such interference.

Thus, devices (such as motors) are often moved to sound proof rooms while analyzing the sounds generated (by the devices). The setting up and maintenance of such sound proof rooms can be very expensive. In addition, the entire testing process may consume unacceptably large periods of time due to the physical movement (to sound proof rooms) and manual testing.

Therefore, what is needed is a quick and efficient method and apparatus to determine the defects in a device.

SUMMARY OF THE INVENTION

The present invention allows a quick determination of whether a device is defective. The determination is performed by generating multiple digital samples representing the sound signals generated by a device. The digital samples are examined using a processor (and any necessary associated software/firmware) to determine whether the device is defective.

As the examination can be implemented substantially using processors, the invention can be implemented at many locations at a minimal cost per unit tested. In addition, errors may be minimized by appropriate design of the testing systems.

The sound signals generated by a device alone may be obtained by subtracting noise components representing noise present in testing environment from sound signals ("incident sound signals") captured by a microphone located close to the device during operation. The subtraction is often referred to as noise cancellation.

By performing noise cancellation, the present invention allows devices to be tested in testing environments without having to resort to sound-proof rooms. As a result, embodiments of the present invention are suited for testing devices such as motors which are generally manufactured in noisy environments.

The digital samples representing the sound signals generated by a device may be processed to convert the sound signals to frequency domain. The resulting frequency spectrum may be analyzed to determine the defects in the device. The frequency spectrum may contain multiple frequencies, each frequency having a corresponding level of intensity. If any of the frequency components contain unacceptable levels of intensity, the device may be determined to be defective. In an embodiment, a fast fourier transform (FFT) is used to generate the frequency spectrum.

According to an aspect of the present invention, a threshold number is maintained associated with each frequency (of interest). Each of the threshold numbers may be compared with the corresponding one of the level of intensity at the respective frequency. The device may be deemed defective if any of the threshold numbers is different from the corresponding one of the levels of intensity (in the generated frequency spectrum).

The threshold numbers may be determined based on inputs provided by an expert. The expert determines whether each one of the test devices is defective by hearing to the sounds generated by each test device. The threshold numbers may be set based on the determination of the expert. Deploying a testing system with other types of devices may merely require changing the threshold numbers.

Further features and advantages of the invention, as well as the structure and operation of various embodiments of the invention, are described in detail below with reference to the accompanying drawings. In the drawings, like reference numbers generally indicate identical, functionally similar, and/or structurally similar elements. The drawing in which an element first appears is indicated by the leftmost digit(s) in the corresponding reference number.

BRIEF DESCRIPTION OF THE DRAWINGS

The present invention will be described with reference to the accompanying drawings, wherein:

FIG. 1 is a flow chart describing a method in accordance with the present invention;

FIG. 2A is a block diagram illustrating an embodiment of a testing system in accordance with the present invention;

FIG. 4B and FIG. 4C are diagrams illustrating the components present in an embodiment of an electric motor;

FIG. 5A is a graph in time domain illustrating the sound signal generated by a non-defective motor;

DETAILED DESCRIPTION OF THE PREFERRED EMBODIMENTS

Figure 2B:
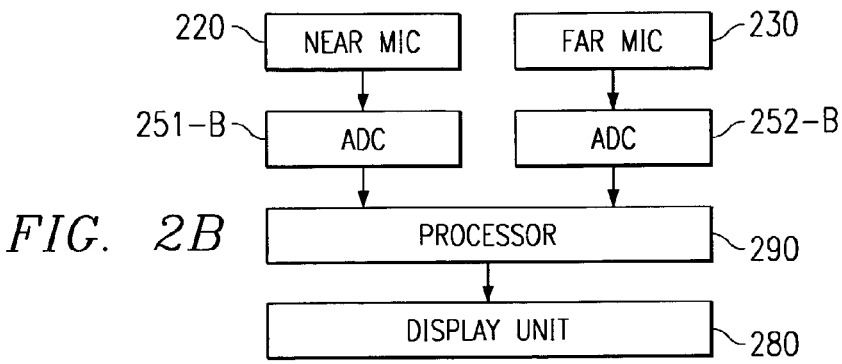
FIG. 2B is a block diagram illustrating an alternative embodiment of a testing system in accordance with the present invention.

1. Overview and Discussion of the Invention

A determination as to whether a device is defective is performed by analyzing the digital representation of sound signals generated by the device during operation. In an embodiment described below, the digital data representing the sound is processed by a digital signal processor (an example of a digital processing system) to transform the sound signal generated by a device into frequency domain. The digital signal processor may be implemented to analyze the resulting frequency spectrum to determine the defects in the device. As digital signal processors can be easily replicated, the present invention can be used to test many devices at several different location with only marginally more cost, while potentially testing each motor accurately.

Another aspect of the present invention obviates the need for sound-proof rooms by capturing the sound ("noise components") generated from sources other than the motor in a testing environment, and removing (cancelling) the noise components from sound ("total noise component") captured close proximity to t he motor. The difference signal is analyzed for defects. As the difference signal represents the sound generated by the motor alone, the testing results may not be affected by the surrounding noise.

For illustration, several aspects of the present invention are described below with reference to a motor manufactured and tested in noisy environments. However, the invention can be implemented to test any device (e.g.,cars, heart beat monitor, etc.) which generates sounds during operation. It should be understood that numerous specific details, relationships, and methods are set forth to provide a full understanding of the invention. One skilled in the relevant art, however, will readily recognize that the invention can be practiced without one or more of the specific details, or with other methods, etc. In other instances, well-known structures or operations are not shown in detail to avoid obscuring the invention. The invention is described first with reference to a method and then with reference to a digital processing system.

2. Method

FIG. 1 is a flow chart depicting a method by which a determination can be made as to whether a motor is defective. The method starts in step 101, in which control immediately passes to step 110. In step 110, the motor (to be tested) is made to operate by switching the motor on. When the motor is switched on, sound signals are generated.

In step 120, digital samples representing the sound signals are generated. In an embodiment, sound signals are first captured in the form of electrical signals in a known way. The electrical signals are then sampled to obtain digital samples.

In step 130, the digital samples may be processed to transform the sound signals into the corresponding frequency domain. In an embodiment, fast fourier transform (FFT) is used for the transformation.

In step 140, the frequency spectrum of the sound signal obtained in step 130 is analyzed. The level of intensity at each frequency may be analyzed to determine the defects present in the motor.

Thus, the method of FIG. 1 may be used to determine the defects in a motor. The description is further continued with reference to an example implementation of the method described above.

3. Testing System

FIG. 2A is a block diagram illustrating the details of an embodiment of testing system 200 used to test motor 210. Testing system 200 is shown containing near microphone 220, far microphone 230, noise cancellation unit 240, converter 250, transformation block 260, comparison logic 270 and display unit 280. Each component is described below in further detail.

Near microphone 220 generates electrical signals (on path 224) corresponding to the incident sound signals. The incident sound signals contain both the sound signals generated by motor 210, and noise components generated from other sources in the testing environment. In general, near microphone 220 should be placed at a distance from motor 210 such that the representative sound signals generated by motor 210 are captured completely.

Far microphone 230 captures noise components present in the manufacturing area to generate a corresponding electrical signal on line 234. Far microphone 230 and near microphone 220 should be situated close enough such that both far microphone 230 and near microphone 220 receive the same levels of sound when the motor is off (non operational). Yet, far microphone 230 should be situated far enough from motor 210 such that far microphone 230 does not capture sound signals generated by motor 210 in substantial respect. One of several commercially available microphones can be used for near microphone 220 and far microphone 230.

Noise cancellation unit 240 operates to cancel the noise components from the sound signals captured by near microphone 220. In the embodiment of FIG. 2, noise cancellation unit 240 subtracts electrical signal generated by near microphone 220 on line 224 from electrical signal generated by far microphone 230 on line 234. Noise cancellation unit 240 generates a corresponding electrical signal (on line 245) which represents the sound generated by motor 210 alone.

Converter 250 samples the electrical signals received on line 245 to generate corresponding digital samples on line 256. The digital samples would ideally represent the sound signals generated by motor 210 alone. While noise cancellation unit 240 is shown as a separate unit prior to converter 250, it should be understood that the noise cancellation can be performed in digital domain after converting the two input electrical signals into digital domain. Such other implementations are also contemplated to be within the scope and spirit of the present invention.

Transformation block 260 processes the digital samples to transform the sound signals (generated by motor 210 alone) into the frequency domain. In an embodiment, fast fourier transform (FFT), well known in the relevant arts, is used for the transformation. The output of transformation block 260 may indicate the intensity at each frequency.

Comparison logic 270 compares the output of transformation block 260 with data samples representing defective and/or non-defective motors to determine whether motor 210 is defective. In one embodiment, comparison logic 270 pre-stores a threshold number associated with each frequency. The threshold number represents the threshold intensity of the sound generated by a non-defective motor at the associated frequency.

Motor 210 may be considered to have a defect if the intensity of sound generated for a particular frequency is different from the corresponding threshold intensity. Thus, comparison logic 270 compares the output of transformation block 260 with the threshold numbers to determine if motor 210 is defective or not. The manner in which the threshold numbers are generated and used is described below with respect to an example.

Display unit 280 may be used to provide a suitable interface for a user while motor 210 is tested. In an embodiment, the sound signal generated by noise cancellation unit 240, the frequency spectrum generated by transformation block 260 and the output of weighted matrix 270 are displayed to the user testing motor 210. By examining the displayed information on display unit 280, a user may decide whether motor 210 is defective or not.

In an alternative embodiment depicted in FIG. 2B, electrical signals generated by near microphone 220 and far microphone 230 are converted before analyzing for defects. Analog to digital converters (ADC) 251-A and 252-B respectively convert electrical signals generated by near microphone 220 and far microphone 230 to generate corresponding digital samples representing respective incident sound signals.

Processor 290 processes digital samples generated by ADC 251-A and 252-B to determine whether the motor is defective. Processor 290 performs tasks such as noise cancellation, transformation, and determination of the presence of any defects in the tested motor. In an embodiment, processor 290 is implemented using TI DSP 5416 (or 5510) available from Texas Instruments Inc., the assignee of the subject patent application.

Display unit 280 may be implemented using a liquid crystal display (LCD). Processor 290 may also use threshold numbers representing defects (defined to include data representing non-defects). The description is continued with respect to the manner in which threshold numbers representing defects may be generated and used.

4. Threshold Numbers Representing Defects

In an embodiment, a weighted matrix may store threshold numbers representing the acceptable level of intensity corresponding to each frequency of sound signal generated by a non-defective motor. Thus, the matrix may contain a number of entries equal to the number of frequencies of interest. The manner in which the weighted matrix may be populated is described below.

An expert is requested to indicate when motors are tested and the values in the weighted matrix are updated based on the output of transformation block 260 for the non-defective motors. Without having to store the output values for each motor, a weight representing the number of samples using which the numbers in the weighted matrix are generated, may be maintained.

When the prior numbers in the weighted matrix are to be updated with the data representing a new non-defective motor, the prior numbers are given a weight proportionate to the number of samples using which the prior numbers are generated. For example, assuming that the weighted matrix contains a number of X for a particular frequency, the number is generated based on Y samples, and that a new non-defective motor has caused a number Z to be generated for the same frequency, the new weighted (W) number may equal $((X \times Y)+(1 \times Z)/(Y+1))$.

Thus, another motor generating a sound component substantially exceeding W for that particular frequency may be determined to be defective.

While the above-illustration is described with reference to data points for non-defective motors, it should be understood that determination can be made using data points for defective motors as well. For example, the weighted matrix (or another matrix) may further contain numbers which indicate the intensity of sound signal frequencies for defective motors, and a tested motor may be discarded if the generated sound signals match the numbers represented by the defective motors.

In general, techniques such as those developed using artificial intelligence can be designed by experimentation to evolve an effective approach for determining defective and non-defective motors.

Thus, when a weighted matrix is based merely on non-defective motors, the level of intensity at each frequency of the sound generated by motor 210 is compared with the corresponding threshold numbers in the weighted matrix. If the level of intensity at a particular frequency is different from the corresponding threshold intensity, motor 210 may be determined to be defective.

As noted above, several features of the present invention can be implemented in a combination of one or more of hardware, software, and firmware. An embodiment implemented in the form of sequences of instructions (software and/or firmware) is described below.

5. Software Implementation

Figure 3:
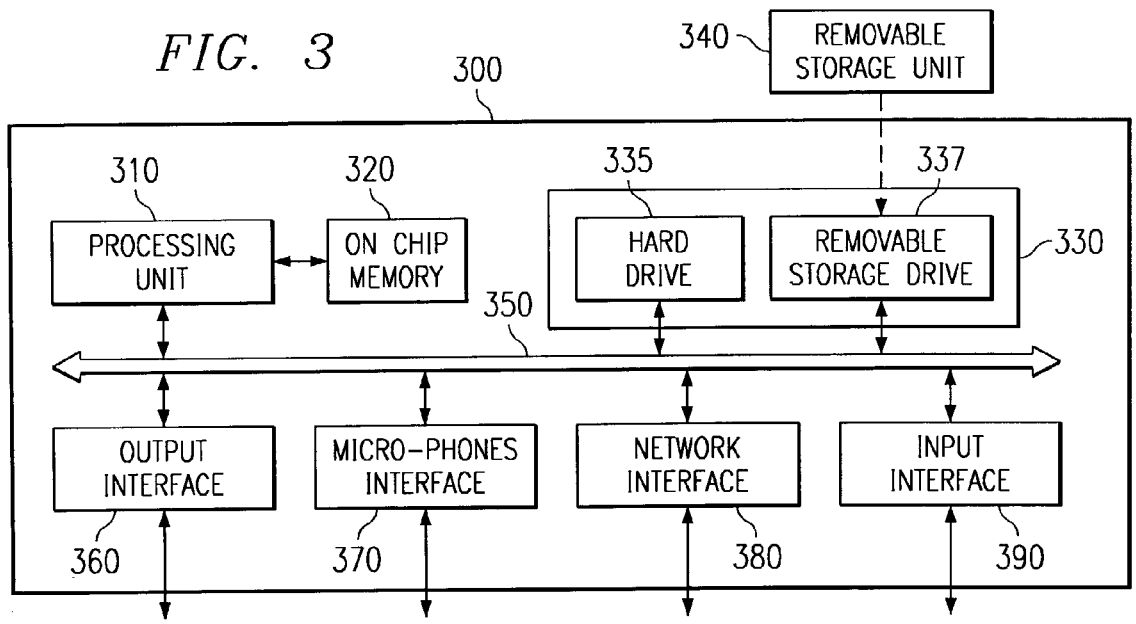
FIG. 3 is a block diagram illustrating an embodiment of the present invention implemented substantially in the form of software.

FIG. 3 is a block diagram illustrating the details of digital processing system 300 in one embodiment. Digital processing system 300 is shown containing processing unit 310, on-chip memory 320, storage 330, output interface 360, micro-phones interface 370, network interface 380 and input interface 390. Each component is described in further detail below.

Output interface 360 provides output signals (e.g., display signals to a LCD, not shown) which can form the basis for a suitable user interface for a user to interact with digital processing system 300. Input interface 390 (e.g., interface with a key-board and/or key-pad, not shown) enables a user to provide any necessary inputs to digital processing system 300.

For example, output interface 360 and input interface 390 can be used, for example, to enable an expert to indicate whether a presently tested motor is defective or not while populating the weighted matrix described above. Similarly, in testing environments, a user may be provided appropriate displays indicating the status of the tested motor.

Micro-phones interface 370 provides a suitable interface to receive electrical signals generated by near micro-phone 220 and far micro-phone 230. Alternatively, the two microphones may be integrated within digital processing system 300. Network interface 380 enables digital processing system 300 to send and receive data on communication networks using protocols such as USB mass storage class. Network interface 380, output interface 360 and input interface 390 can be implemented in a known way.

On-chip memory 320 and/or storage 330 may be referred to as a memory. On-chip memory 320 may receive instructions and data from processing unit 310. In an alternative embodiment, a conventional random access memory (RAM) may be used instead of or in addition to on-chip memory 320.

Secondary memory 330 may contain units such as hard drive 335 and removable storage drive 337(e.g., compact flash, MMC card, etc.). The threshold levels of intensity (weighted matrix) at corresponding frequencies that may be present in the sound generated by a non-defective motor may be stored in secondary memory 330. Secondary memory 330 may store the software instructions and data, which enable digital processing system 300 to provide several features in accordance with the present invention.

Some or all of the data and instructions (software routines) may be provided on removable storage unit 340, and the data and instructions may be read and provided by removable storage drive 337 to processing unit 310. Floppy drive, magnetic tape drive, CD-ROM drive, DVD Drive, Flash memory, removable memory chip (PCMCIA Card, EEPROM) are examples of such removable storage drive 337.

In an embodiment, data representing various threshold values is present in Linear Flash or EEPROM, and the stored data is used by digital processing system 300 when testing various devices. The data (threshold values) may merely need to be replaced to enable digital processing system 300 to test some other type of devices.

Processing unit 310 may contain one or more processors. Some of the processors can be digital signal processors which execute instructions provided from on-chip memory 320. Some can be special purpose processors adapted for specific tasks. The special purpose processors may also be provided instructions from on-chip memory 320.

In general, processing unit 310 reads sequences of instructions from various types of memory medium (including on-chip memory 320, storage 330 and removable storage unit 340), and executes the instructions to provide various features of the present invention described above. In particular, a set of software instructions may be designed to analyze the digital samples representing the sound signals generated by a motor to determine whether the motor is defective or not. Another set of signals may be used to cancel the noise components generated by far microphone 230 from the incident sound signals generated by near microphone 220.

Thus, digital processing system 300 may be implemented substantially in software to determine whether a motor is defective. In an embodiment, digital processing system 300 is implemented using product number DSP 5416 (or 5510) available from Texas Instruments, Inc., the assignee of the subject patent application. The description is continued with reference to examples of defective motors and non defective motors.

6. Examples

Figure 4A:
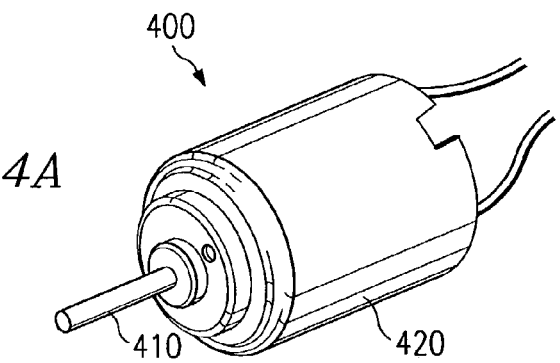
FIG. 4A is a diagram illustrating the details of an embodiment of an electric motor.

FIG. 4A is a block diagram illustrating the details of an embodiment of electric motor 400. Electric motor 400 is shown containing shaft 410 and metal casing 420. Motor 400 may be fitted to devices such as fans, etc., by shaft 410. FIG. 4B depicts metal casing 420, and electromagnets 430-A and 430-B as separate components. FIG. 4C depicts the components as would be placed inside the assembled components of (metal casing 420 and electromagnets 430-A and 430-B) FIG. 4B. Coils 440 are shown present between electromagnets 430-A and 430-B.

The manner in which sound generated by a motor can be analyzed to determine the defects is described with reference to the graphs of FIGS. 5A through 5F. The analysis is performed for the motor operating at a speed of 7500 rpm (rotations per minute). Each graph is described in further detail below.

Figure 5B:
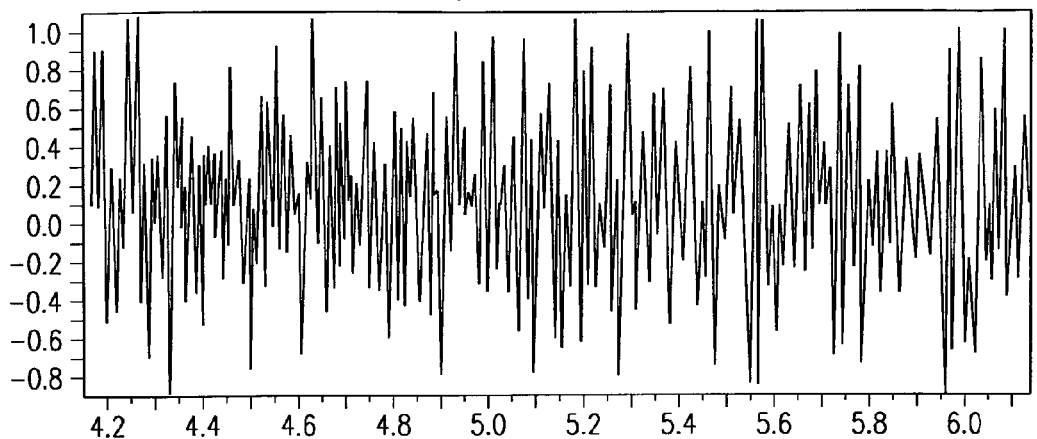
FIG. 5B is a graph in time domain illustrating the sound signal generated by a defective motor.
Figure 5C:
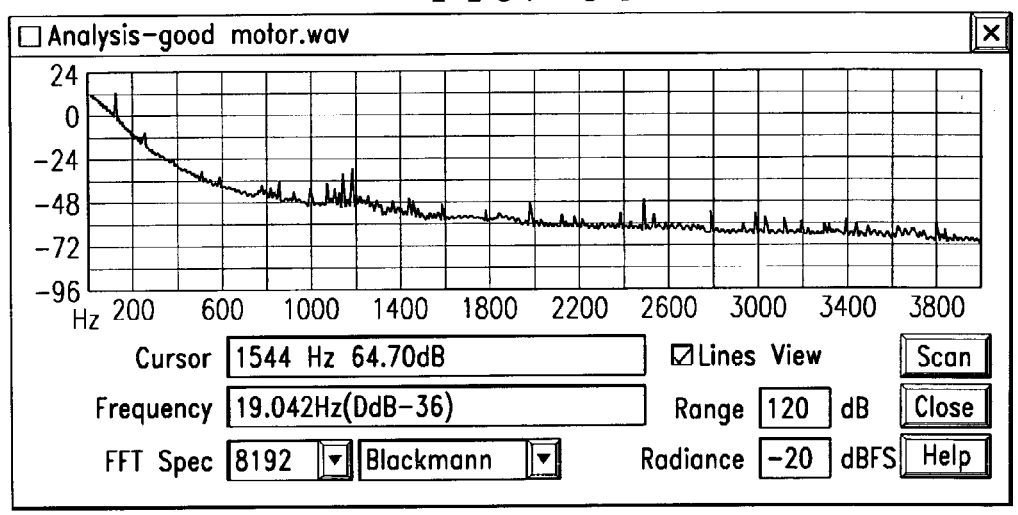
FIG. 5C is a graph illustrating a frequency spectrum of the sound signal generated by a non-defective motor.

FIGS. 5A and 5B are graphs illustrating the sound signals generated by a good (non defective) motor and a defective motor respectively. The graphs of FIG. 5A and 5B are in the time domain, i.e., the x-axis represents time and the y-axis represents the amplitude of the respective sound signals. FIGS. 5C is a graph of the sound signals of FIG. 5A (non-defective motor) converted into frequency domain using, for example, the fast fourier transform (FFT). Similarly, FIG. 5D is a graph of the sound signals of FIG. 5B (defective motor) converted into frequency domain.

Figure 5D:
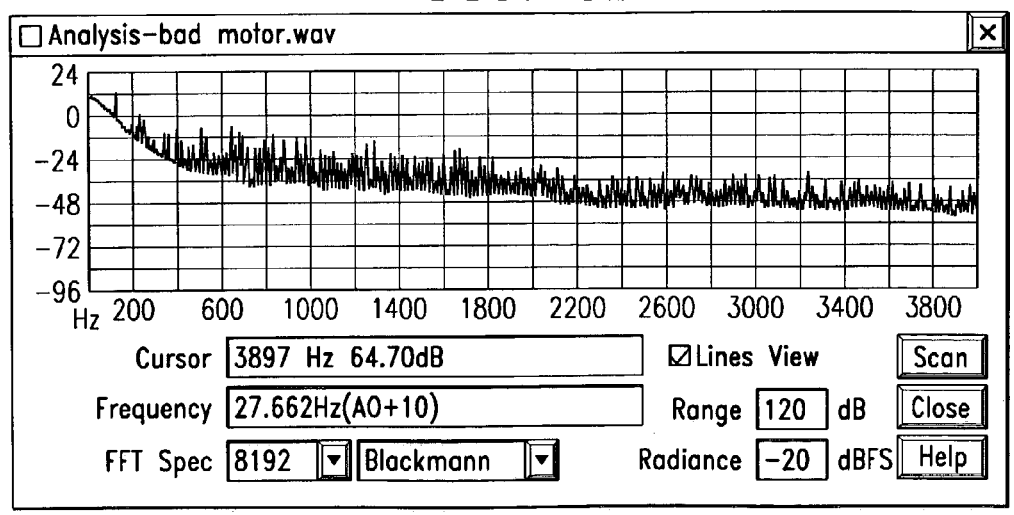
FIG. 5D is a graph illustrating a frequency spectrum of the sound signal generated by a defective motor.
Figure 5E:
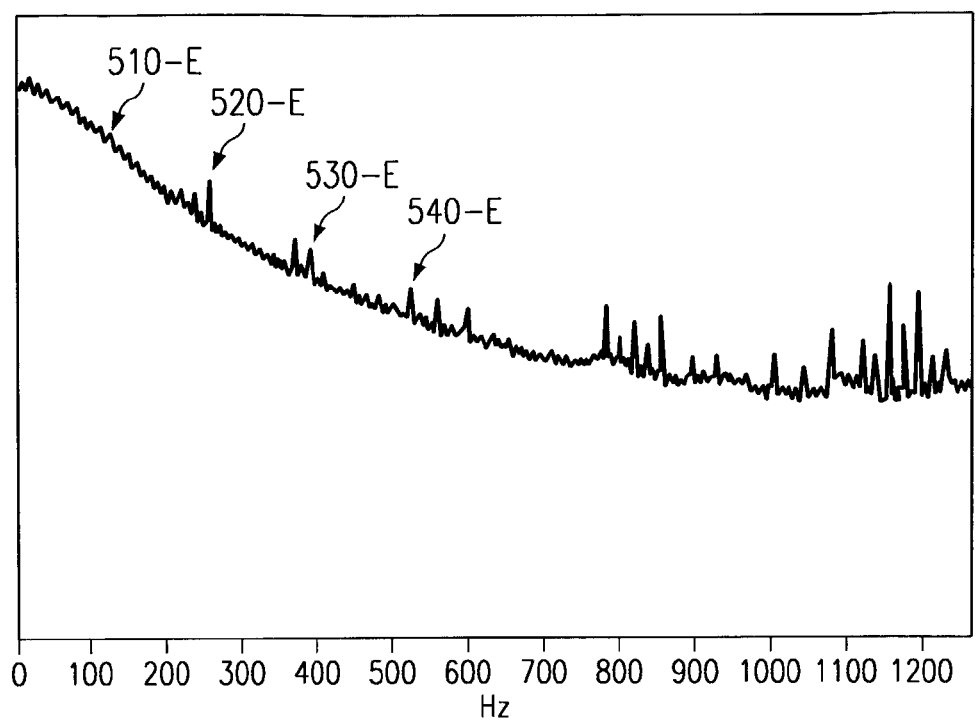
FIG. 5E is a graph illustrating the sound intensity of some of the frequencies generated by a non-defective motor.
Figure 5F:
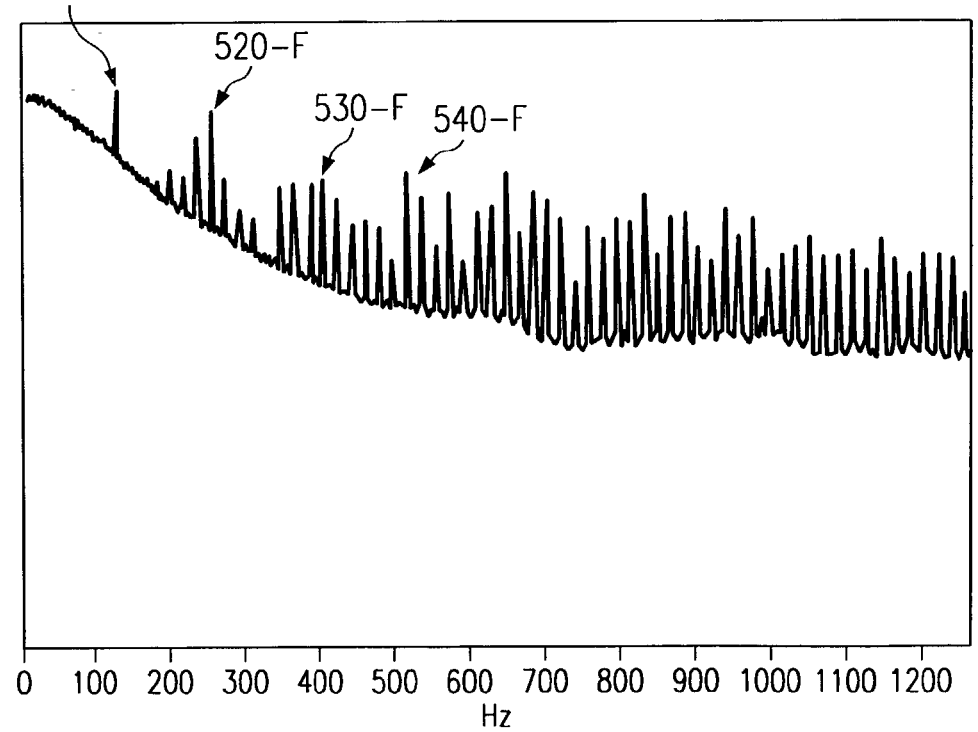
FIG. 5F is a graph illustrating the sound intensity of some of the frequencies generated by a defective motor.

In both FIGS. 5C and 5D, the x-axis represents frequency in Hertz (Hz) and the y-axis represents intensity of the sound in decibels (dB). The manner in which the frequency domain graphs can be analyzed for defects is illustrated below with reference to FIGS. 5E and 5F. FIGS. 5E and 5F together contain the respective frequency domain graphs in the frequency range 0 to 1200 Hz for the defective and non-defective motors, and illustrate the non-defective and defective features respectively. Only four representative points (510-E, 520-E, 530-E and 540-E of FIG. 5E) are considered and described below for clarity and conciseness.

With reference to point 510-E of FIG. 5E, a thin peak is shown at frequency point 510-E. The point approximately equals 125 Hz representing a rotation rate of 7500 rotations per minute (RPM). The thin peak indicates that motor 400 is operating at 125 Hz. The low level of intensity indicate that shaft 410 is sliding in the metal casing 420. The level of intensity at frequency point 510-E is acceptable, and thus is not considered a defect.

In the corresponding point 510-F of FIG. 5F, a thick peak is shown at frequency point 510-F. The level of intensity around point 510-F is more than that at point 510-E of FIG. 5E. The higher level of intensity indicates that shaft 410 is hitting metal casing 420. Shaft 410 may hit metal casing 420 when metal casing 420 is oval in shape and not circular.

It may be noted that the high level of intensity is in a narrow range around point 510-F. The range appears as a 'thick peak'. The thick peak results from the fact that motor 400 may not be operating at 125 Hz precisely, but over a range of frequencies (e.g. 124 HZ–126 Hz). In general, it may be necessary to check for high levels of intensity in a narrow range of frequencies around each frequency of interest.

With reference to point 520-E of FIG. 5E, a low level of intensity is shown at frequency point 520-E (about 250 Hz, twice the frequency of motor 400). The low level of intensity indicates that electromagnets 430-A and 430-B are located at an acceptable distance from metal casing 420 of motor 400.

At the corresponding frequency point 520-F in FIG. 5F, a high level of intensity is shown. The high level of intensity indicates that electromagnets 430-A and 430-B are located very close metal casing 420 which may be due to a dent present in metal casing 420.

With reference to frequency point 540-E of FIG. 5E, a low level of intensity is shown at frequency point 540-E (about 400 Hz). The low level of intensity indicates that electromagnets 430-A and 430-B are not touching metal casing 420 when motor 400 is operational. Thus, it can be concluded that metal casing 420 is circular in shape.

At the corresponding point 540-F of FIG. 5F, a high level of intensity is shown. The high level of intensity indicates that both electromagnets 430-A and 430-B are touching metal casing 420. Such a situation arises when metal casing 420 is oval in shape. Electromagnets 430-A and 430-B may touch metal casing 420 at two sides, hence frequency point 540-F is about four times the frequency of motor 400.

With reference to point 530-E of FIG. 5E, a low level of intensity is shown at frequency point 530-E (about 375 Hz which is thrice the frequency of motor 400). The low level of intensity is referred to as harmonics and exists due to the frequencies present at points 510-E (125 Hz) and 520-F (250 Hz).

Similarly, in FIG. 5F harmonics exist at the corresponding frequency point 530-F (375 Hz). It may be observed that harmonics are present at several other points in FIG. 5F. The harmonics are generally formed due to frequencies 125 Hz, 250 Hz, 375 Hz and 500 Hz present at frequency points 510-F, 520-F, 530-F and 540-F respectively. The harmonics typically do not signify any defect in motor 400 and may be ignored.

In general only the frequencies within a frequency range of interest may need to be analyzed. The frequency range of interest generally has an upper limit equal to a multiple of the base rotational frequency of motor 400. The multiple depends on the base frequency at which sounds may manifest when defects of interest are present. In the example above, the multiple equals 4 as sounds are caused four times in a rotation (500 Hz) in the defect corresponding to points 540-F.

In general, an expert's input may be used to determine the specific frequencies of interest and the associated threshold levels of intensity. The defects can then be determined as described above.

7. Conclusion

While various embodiments of the present invention have been described above, it should be understood that they have been presented by way of example only, and not limitation. Thus, the breadth and scope of the present invention should not be limited by any of the above described exemplary embodiments, but should be defined only in accordance with the following claims and their equivalents.

What is claimed is:

1. A method for determining whether a device is defective, said method comprising:
    generating a plurality of digital samples representing a plurality of sound signals generated by said device; and
    examining said plurality of digital samples to determine whether said device is defective including:
        processing said digital samples to convert said plurality of sound signals to frequency domain, wherein said processing generates a frequency spectrum including a plurality of frequencies and a corresponding plurality of levels of intensity;
        maintaining a threshold number associated with each of said plurality of frequencies; and
        analyzing said frequency spectrum to determine said defects in said device comprising:
            comparing each of said threshold numbers with a corresponding one of said plurality of levels of intensity, and
            determining whether said device is defective according to said comparing.

2. The method of claim 1, further comprising:
    receiving a plurality of noise components representing noise present in testing environment, wherein said plurality of noise components are generated by sources other than said device;
    receiving a plurality of incident sound signals generated by a microphone located close to said device during operation; and
    subtracting said plurality of noise components from said plurality of incident sound signals to generate said plurality of sound signals.

3. The method of claim 1, wherein said processing comprises using a fast fourier transform (FFT) to generate said frequency spectrum.

4. The method of claim 1, wherein said determining comprises concluding that said device is defective if any of said threshold numbers is different from said corresponding one of said plurality of levels of intensity.

5. The method of claim 1, further comprising determining values corresponding to said threshold numbers based on inputs provided by an expert, wherein said expert determines whether each one of a plurality of test devices is defective or not by hearing to the sounds generated by each of said plurality of test devices and provides said inputs.

6. The method of claim 5, further comprising replacing said threshold numbers with a new set of threshold of numbers to test a different type of device.

7. The method of claim 5, further comprising enabling a person to indicate whether said device is defective or not, and updating said threshold numbers according to whether said device is defective or not.

8. The method of claim 1, wherein said device corresponds to a motor, wherein said motor comprises a shaft, a casing, an electro-magnet and a coil.

9. A computer readable medium carrying one or more sequences of instructions for causing a system to determine whether a device is defective, wherein execution of said one or more sequences of instructions by one or more processors contained in said system causes said one or more processors to perform the actions of:
    receiving a plurality of digital samples representing a plurality of sound signals generated by said device; and
    examining said plurality of digital samples to determine whether said device is defective including:
        processing said digital sample to convert said plurality of sound signals to frequency domain, wherein said processing generates a frequency spectrum including a plurality of frequencies and a correspondig plurality of levels of intensity;
        maintaining a threshold number associated with each of said plurality of frequencies; and
        analyzing said frequency spectrum to determine said defects in said device comprising:
            comparing each of said threshold numbers with a corresponding one of said plurality of levels of intensity, and
            determining whether said device is defective according to said comparing.

10. The computer readable medium of claim 9, further comprising:
    receiving a plurality of noise components representing noise present in testing environment, wherein said plurality of noise components are generated by sources other than said device;
    receiving a plurality of incident sound signals generated by a microphone located close to said device during operation; and
    subtracting said plurality of noise components from said plurality of incident sound signals to generate said plurality of sound signals.

11. The computer readable medium of claim 9, wherein said processing comprises using a fast fourier transform (FFT) to generate said frequency spectrum.

12. The computer readable medium of claim 9, wherein said determining comprises concluding that said device is defective if any of said threshold numbers is different from said corresponding one of said plurality of levels of intensity.

13. The computer readable medium of claim 9, further comprising:
receiving from an expert a plurality of inputs representing whether each one of a plurality of test devices is defective or not; and
determining values corresponding to said threshold numbers based on said plurality of inputs.

14. The method of claim 13, further comprising replacing said threshold numbers with a new set of threshold of numbers to test a different type of device.

15. The method of claim 13, further comprising enabling a person to indicate whether said device is defective or not, and updating said threshold numbers according to whether said device is defective or not.

16. The computer readable medium of claim 9, wherein said device corresponds to a motor, wherein said motor comprises a shaft, a casing, an electro-magnet and a coil.

17. A digital processing system for determining whether a device is defective, said digital processing system comprising:
means for receiving a plurality of digital samples representing a plurality of sound signals generated by said device; and
means for examining said plurality of digital samples to determine whether said device is defective including:
means for processing said digital samples to convert said plurality of sound signals to frequency domain, wherein said processing generates a frequency spectrum including a plurality of frequencies and a corresponding plurality of levels of intensity;
means for maintaining a threshold number associated with each of said plurality of frequencies; and
means for analyzing said frequency spectrum to determine said defects in said device comprising:
means for comparing each of said threshold numbers with a corresponding one of said plurality of levels of intensity, and
means for determining whether said device is defective according to said comparing.

18. The digital processing system of claim 17, further comprising:
means for receiving a plurality of noise components representing noise present in testing environment, wherein said plurality of noise components are generated by sources other than said device;
means for receiving a plurality of incident sound signals generated by a microphone located close to said device during operation; and
means for subtracting said plurality of noise components from said plurality of incident sound signals to generate said plurality of sound signals.

19. The digital processing system of claim 17, wherein said means for processing uses a fast fourier transform (FFT) to generate said frequency spectrum.

20. The digital processing system of claim 17, wherein said means for determining concludes that said device is defective if any of said threshold numbers is different from said corresponding one of said plurality of levels of intensity.

21. The digital processing system of claim 17, further comprising means for determining values corresponding to said threshold numbers based on inputs provided by an expert, wherein said expert determines whether each one of a plurality of test devices is defective or not by hearing to the sounds generated by each of said plurality of test devices and provides said inputs.

22. The digital processing system of claim 17, wherein said device corresponds to a motor, wherein said motor comprises a shaft, a casing, an electro-magnet and a coil.

* * * * *